United States Patent
Ecanow

(10) Patent No.: US 7,229,967 B2
(45) Date of Patent: Jun. 12, 2007

(54) OXYGENATED ALBUMIN FOR USE AS BLOOD AND BLOOD EXTENDER

(75) Inventor: Bernard V. Ecanow, Long Grove, IL (US)

(73) Assignee: Hunter Research Corporation, Long Grove, IL (US)

( * ) Notice: Subject to any disclaimer, the term of this patent is extended or adjusted under 35 U.S.C. 154(b) by 185 days.

(21) Appl. No.: 10/987,787

(22) Filed: Nov. 12, 2004

(65) Prior Publication Data

US 2006/0105056 A1 May 18, 2006

(51) Int. Cl.
*A61K 38/38* (2006.01)
*A61K 33/40* (2006.01)
*C07K 14/765* (2006.01)
*C07K 14/77* (2006.01)

(52) U.S. Cl. .................. 514/12; 424/613; 530/363; 530/367

(58) Field of Classification Search ............... None
See application file for complete search history.

(56) References Cited

U.S. PATENT DOCUMENTS 4,439,424 A    3/1984   Ecanow et al.
5,948,609 A    9/1999   Carter et al.
6,770,052 B2   8/2004   Hill et al.

OTHER PUBLICATIONS

PCT International Search Report by the European Patent Office for International Application No. PCT/US2005/034797 dated Jun. 2, 2006 (3 pages).
"Secretion of Medullipin I by Isolated Kidneys Perfused Under Elevated Pressure" Clinical and Experimental Pharmacology and Physiology, by E. E. Muirhead et al., vol. 18, No. 6, Jun. 1991 (pp. 409-417).

*Primary Examiner*—Robert A. Wax
(74) *Attorney, Agent, or Firm*—Marshall, Gerstein & Borun LLP

(57) ABSTRACT

The compositions described herein comprise oxygenated albumin in an aqueous sterile physiological or serum solution. The albumin is oxygenated to increase the oxygen content up to $O_2$ saturation with clinically useful oxygen gas. The preferred oxygen-saturated preparations, containing albumin in concentrations from about 5% w/v to about 25% w/v, are useful as clinical resuscitation preparations that release oxygen in a pattern similar to the release of oxygen by whole blood.

26 Claims, 1 Drawing Sheet

OXYGENATED ALBUMIN FOR USE AS BLOOD AND BLOOD EXTENDER

FIELD OF THE INVENTION

The present invention is directed to an aqueous oxygenated albumin composition that is useful as a human blood substitute or human blood extender, methods of manufacturing the oxygenated albumin composition, and methods of treating abnormal conditions therewith. The oxygenated albumin aqueous compositions, described herein, are capable of dissolving and transporting high concentrations of hydrophobic molecules, particularly oxygen, and releasing the oxygen in a manner similar to the release of oxygen by hemoglobin. The compositions possess many of the same physiological capabilities of whole human blood.

BACKGROUND

Albumin makes up about 62 percent of the total protein of human plasma, about 80 percent of the plasma colloidal pressure, and has been used since World War II, and continues to be used, in maintaining or restoring human plasma volume. The Standard Army and Navy Package of Dried Plasma is bulky, and therefore concentrated human serum albumin was developed to meet the needs of such groups for a concentrated blood derivative. Serum albumin has at least two known functions: it maintains the colloidal osmotic pressure of the blood and plays a role in the nutrition of the tissues. Neither plasma nor albumin solutions, however, can act as a total replacement for human blood indefinitely since they cannot supply the necessary hemoglobin and other essential blood protein constituents. However, human serum albumin is used effectively in concentrations up to about 25% by volume, and has advantages over solutions of salts and glucose in establishing safe osmotic pressure, particularly in emergency blood loss situations, e.g., in the treatment of shock hemorrhage, and other conditions associated with substantial blood loss.

Advantageously, human serum albumin can be dried to reduce volume and can be reconstituted, preferably with sterile water, prior to administration, e.g., by injection. Human serum albumin is available, for example, in 100 c.c. bottles containing 25 gm. of albumin, which is equivalent in osmotic effect to 500 c.c. of citrated plasma. Human serum albumin also is available from Bayer Healthcare, as PLASBUMIN®-25, in 20 ml. vials. PLASBUMIN®-25 is made from pooled human venous plasma using the Cohn cold ethanol fractionation process to produce a sterile solution of albumin in an aqueous diluent that is stabilized with 0.02M sodium caprylate and 0.02M acetylptophan. The approximate sodium content is 145 mEq./L., contains no preservative, and is administered intravenously.

Albumin solutions are stable, permitting transportation without refrigeration, ready for instant use, and, as with plasma, no preliminary cross-matching is necessary. A 25% w/v aqueous solution of albumin is approximately isoviscous with whole blood.

It has long been recognized in clinical medicine that an acceptable oxygen carrying and releasing resuscitation product is needed. There is currently no satisfactory non-blood product with these properties in clinical use.

Two general approaches to making such an oxygen-carrying product have been attempted either through the use of oxygen binding hemoglobin or the use of a nonpolar, fat-soluble, hydrophobic solvent system.

A third approach, that of using an aqueous system as an oxygen carrying solvent would presumably be obviated by the fact that the oxygen molecule is less than 2% soluble at physiologic temperatures in an electrolytic aqueous system such as human serum.

In the case of the hemoglobin systems the use of naked hemoglobin is toxic. Polymerized hemoglobin and hemoglobin bound to various bases, such as starch or other polymers, have proven both unstable and ineffective.

Efforts to encapsulate hemoglobin have been attempted using coacervates and liposomes. During the processing and use of liposomes the hemoglobin tends to leak from the encapsulating liposome. The liberated free hemoglobin results in the known toxicities of naked hemoglobin. Additionally, the hemoglobin that remains in the liposome does not release oxygen in the patient as needed. Some 30 years of efforts in this direction have proven unsatisfactory. The use of liposome or polymerized hemoglobin after years of trials has not been shown to be clinically useful.

The use of coacervates containing hemoglobin demonstrated both manufacturing and clinical problems. Manufacturing efforts resulted in difficulties with achieving appropriate particle sizes and with methemoglobin formation. While the toxicities of naked hemoglobin were overcome, the resultant product had difficulties carrying and releasing oxygen in a clinically effective manner.

A nonpolar solvent system can dissolve nonpolar oxygen molecules. Many such products over the past sixty years, such as the perfluorocarbons, while effective at dissolving oxygen, have clinically proven to be toxic, unstable, and ineffective. Indeed, toxicity could be anticipated from such nonpolar systems, since many of the organs in the body are nonpolar themselves. Thus the tactic of infusing large volumes of the perfluorocarbon-type nonpolar solvent systems for carrying oxygen would tend to be absorbed by and disrupt the body's organs. A typical example is that the liver, which is nonpolar in character, absorbs the perfluorocarbon with resultant hepatomegaly and liver failure. The nonpolar solvents cannot dissolve polar drugs or vitamins or other desirable polar chemical agents.

The principal users of human serum albumin are surgeons. The indications for prescribing albumin include acute hypovolemia associated with surgery, trauma, hypoproteinemia, with or without edema, adult respiratory distress syndrome (ARDS), transplantations; obligatory extracellular space imbalance, as in severe burns, respiratory distress syndrome, and heart-lung machine pump priming. In coronary artery bypass surgery, the heart-lung machine is primed without the use of blood by using 1,000 c.c. of Ringer's lactate solution, 300 c.c. of 25% salt-poor albumin, 66.7 mEq. sodium bicarbonate or 250 c.c. trishydroxy-methylaminomethane, and 20 gm. of mannitol. Indications for use of human serum albumin by internists include acute gastrointestinal hemorrhage, renal dialysis, erythrocyte resuspension, sequestration of protein-rich fluids and several chronic conditions such as malabsorption, cirrhosis, acute liver failure, nephrosis, neonatal hemolytic disease, cerebral vascular accidents and ischemia.

The oxygenated albumin described herein preferably is oxygenated human serum albumin, and is more useful than non-oxygenated human serum albumin in the treatment of all of the above recited indications for prescribing albumin. The oxygenated albumin can be delivered to the human body either as a solution, or as a suspension of oxygenated albumin in sterile water.

The compositions and methods described herein stem from the unexpected finding that aqueous solutions containing up to 25% w/v concentrated amounts of hydrophilic albumin can indeed act as nonpolar solvents for delivery of oxygen and other nonpolar compounds. The most clinically useful example of this is the fact that aqueous human albumin solutions of less than 3% w/v can carry very little oxygen. However, at concentrations of around 25% w/v, human albumin in water can dissolve clinically significant quantities of oxygen. Further, as the aqueous albumin solution dilutes in the blood stream, it releases the oxygen in a manner similar to that displayed by whole human blood. No hemoglobin is required in this preparation. No other solvent system exhibits these properties except whole blood.

U.S. Pat. No. 6,777,052 discloses a plastic container for containing albumin solution having an albumin concentration of 1 to 500 mg/ml. The oxygenated albumin solutions described herein can be used with such a container in oxygenated albumin concentrations of 1 to 500 mg/ml, or any other oxygen-impermeable package, e.g., glass bottles, can be used to contain the oxygenated albumin compositions described herein.

SUMMARY

The preferred compositions described herein comprise oxygenated albumin in an aqueous sterile physiological or serum solution. The albumin is oxygenated to increase the oxygen content up to $O_2$ saturation with clinically useful oxygen gas. The preferred oxygen-saturated preparations, containing albumin in concentrations from about 5% w/v to about 25% w/v, are useful as clinical resuscitation preparations that release oxygen in a pattern similar to the release of oxygen by whole blood.

Since all chemicals contained in the compositions described herein are endogenous to the body and are used individually in various clinical situations, no toxicity has been found or is anticipated.

Preparations containing albumin concentrations from 25% w/v to 50% w/v and higher can contain large quantities of dissolved oxygen in a gel state. These gel oxygenated albumin preparations can release oxygen in situations in which $O_2$ is required other than as a resuscitation fluid.

BRIEF DESCRIPTION OF THE DRAWING

The drawing is a graph showing the predicted oxygen release of the oxygenated albumin described herein compared to the oxygen release of hemoglobin.

DETAILED DESCRIPTION OF THE INVENTION

Figure 1:
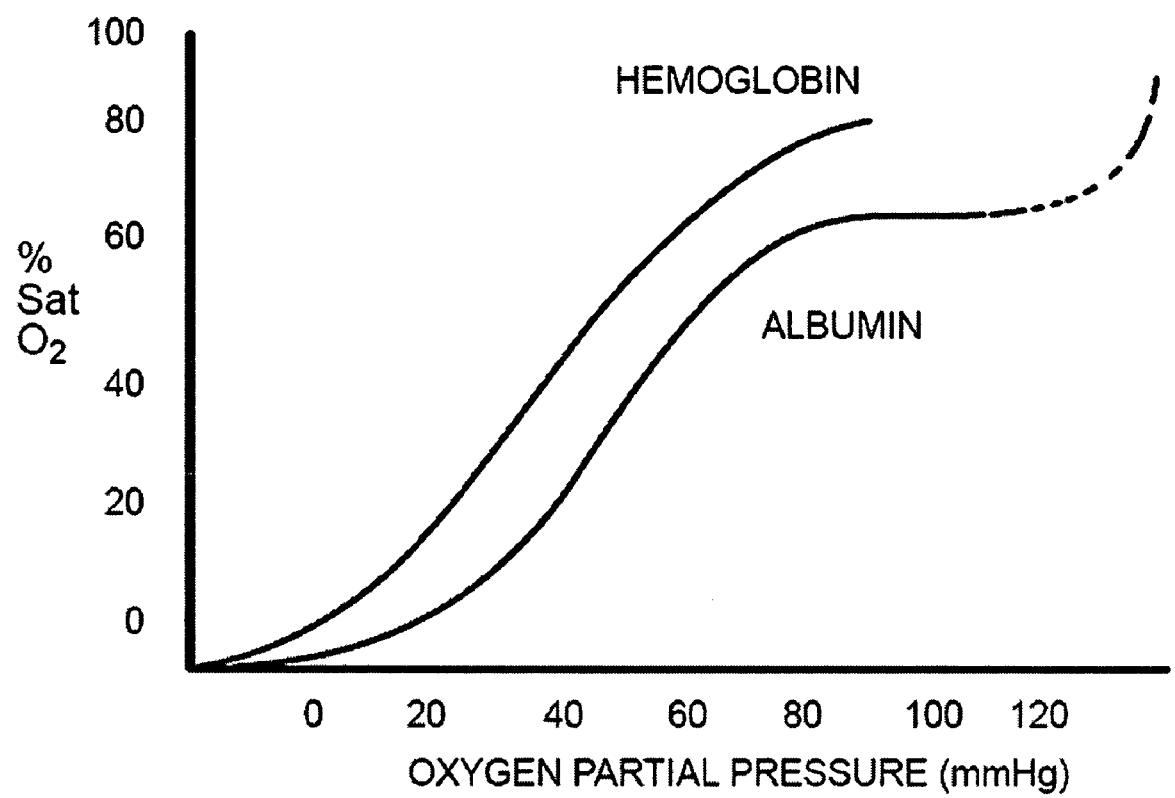

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The oxygenated albumin solutions described herein are useful as an acceptable resuscitation fluid indicated for use in the clinical setting of hypotension or hemorrhage in which $O_2$ is desired. It is an additional object of the invention to provide a convenient method for preparing a readily available resuscitation fluid that contains a supply of oxygen and water-soluble essential chemicals.

In addition to being a resuscitation fluid, other water-soluble additives can be included in oxygenated albumin composition, in addition to carrying clinically significant amounts of oxygen. Further, the oxygen is released in the blood stream in a manner similar to that of oxygen release from whole blood.

In addition this invention has the unique ability (except for whole blood) to dissolve and release soluble polar and nonpolar essential and clinic useful chemicals.

The compositions and methods described herein provide an oxygen-carrying aqueous colloidal resuscitation fluids that carry oxygenated albumin in a sterile aqueous vehicle. The albumin is oxygenated to achieve at least a 1% v/v increase in the albumin oxygen content, up to a preferred oxygen saturation of the albumin. Upon intravenous injection and subsequent dilution in the blood stream; the oxygen is released in a non-linear manner that is similar to the non-linear manner of oxygen release from hemoglobin in whole blood, as shown in the drawing.

As indicated in the drawing, hemoglobin releases oxygen to the blood stream in a standard sigmoid curve wherein the partial pressure of oxygen varies with percent oxygen saturation of the hemoglobin. The albumin curve mirrors the physiologic behavior of whole blood as the albumin is diluted from 25% w/v to 5% w/v.

The colloidal albumin compositions can be prepared by dispersing from 5% to 50% weight to volume of human serum albumin in distilled water containing, for example, 0.9% weight to volume sodium chloride. The albumin is permitted to become completely hydrated and then stirred to give a uniform dispersion of ingredients. The preparation is in a container that includes a gas bubble inlet tube. Oxygen gas then is introduced slowly into the aqueous albumin solution preparation and this oxygenation process preferably is continued until the liquid system is 100% saturated with the oxygen gas. The composition can then be stored at temperatures that preferably do not exceed 30° C. An alternative method of preparing the oxygenated albumin compositions is to purchase a readily obtainable albumin (human) 5% w/v to 25% w/v USP resuscitation composition that is clinically used as a blood volume extender. To this commercial preparation, oxygen is infused, preferably until the preparation is 100% saturated with $O_2$ gas.

Important advantages of the oxygenated albumin compositions described herein include the following: the albumin is readily available, the ingredients individually are currently in routine clinical use with an excellent safety profile, and all substances contained in the compositions occur naturally in the mammalian body. The equipment and methods required for oxygenating the albumin solution are routinely used in the pharmaceutical industry. The chief advantage of the compositions and methods described herein is that upon intravenous injection or transfusion, the oxygenated albumin composition can establish and maintain the desired osmotic pressure while supplying the needed oxygen to the patient. In addition to supplying oxygen, the composition can, at the same time, supply needed pharmacological and physiological oil-soluble and/or water-soluble compounds. No other resuscitation fluid, besides whole blood, can perform in this manner.

The compositions described herein can transport and transfer to the human body a number of other materials in addition to oxygen, such as carbon dioxide, therapeutic agents, physiological entities, nutrients and enzymes.

The basic unoxygenated albumin preparation, as currently in clinical use as a blood volume extender, can diffuse and pass through the circulatory system, and are metabolized and excreted without a problem. Accordingly, the oxygenated version of the albumin described herein, using the same albumin but now transporting and providing oxygen, has no difficulties with its behavior in-vivo.

The amount, route, rate, temperature, storage, equipment and routine of administration necessary for the use of the oxygenated albumin compositions described herein are equivalent to that of the non-oxygenated albumin blood extenders currently in use.

EXPERIMENT

The following in-vitro experiment was conducted to test the oxygen carrying capacity of oxygenated human serum albumin.

The oxygen carrying capacity of albumin compositions having increasing albumin concentrations was shown by the following in-vitro experiment. Four aqueous albumin compositions were tested as follows: (1) 3% albumin, (2) 10% albumin, (3) 25% albumin (Bayer Corporation) PLASBUMIN®-25 and (4) 50% albumin. Compositions used as controls were as follows (5) saline solution and (6) saline solution with 5% stroma free hemoglobin. Oxygen was bubbled through each preparation for 60 minutes at 37° C. The results were as follows:

|   | Substance | Oxygen Uptake v/v |
|---|---|---|
| 1. | 3% Albumin | 4% |
| 2. | 10% Albumin | 19% |
| 3. | 25% Albumin | 64% |
| 4. | 50% Albumin | 78% |
| 5. | Saline solution | 0.5% |
| 6. | Saline with 5% hemoglobin | 4% |

A similar experiment using egg albumin would provide similar results.

What I claim and desire to protect by Letters Patent:

1. A method for making a resuscitation fluid containing dissolved oxygen gas which comprises the steps of
   (a) dispersing about 10% w/v to about 50% w/v human albumin into sterile water to form an aqueous albumin composition; and
   (b) bubbling oxygen gas through the aqueous albumin composition of step (a) to form oxygenated albumin having an oxygen content that is increased by at least 1% v/v.

2. The method of claim 1, further including the step of storing the oxygenated albumin at a temperature not exceeding about 26° C.

3. The method of claim 1 wherein the concentration of albumin in the aqueous albumin composition is about 10% w/v to about 25% w/v.

4. The method of claim 1 wherein the concentration of albumin in the aqueous albumin composition is about 25% w/v to about 50% w/v.

5. The method of claim 1 wherein the concentration of albumin in the aqueous albumin composition is 12.5% w/v.

6. The method of claim 1 further including the step of adding a vitamin to the resuscitation fluid.

7. The method of claim 1 further including the step of adding an antibiotic to the resuscitation fluid.

8. The method of claim 1 further including the step of adding a nutrient to the resuscitation fluid.

9. The method of claim 1 further including the step of adding a mineral to the resuscitation fluid.

10. A composition comprising an aqueous solution and/or suspension of oxygenated albumin containing 10% w/v to 50% w/v oxygenated albumin.

11. The composition of claim 10 wherein the concentration of albumin in the aqueous albumin composition is about 10% w/v to about 25% w/v.

12. The composition of claim 10 wherein the concentration of albumin in the aqueous albumin composition is about 25% w/v to about 50% w/v.

13. The composition of claim 10, wherein the albumin comprises human serum albumin.

14. The composition of claim 10, wherein the albumin comprises chicken egg albumin.

15. A method of delivering oxygen to a mammal comprising injecting the mammal with an aqueous composition containing water and 10% w/v to 50% w/v oxygenated albumin.

16. The method of claim 15 wherein the concentration of albumin in the aqueous albumin composition is about 10% w/v to about 25% w/v.

17. The method of claim 15 wherein the concentration of albumin in the aqueous albumin composition is about 25% w/v to about 50% w/v.

18. A method of increasing a blood volume of a hemorrhaging mammal comprising injecting the mammal with an aqueous composition comprising water and about 10% w/v to about 50% w/v oxygenated albumin.

19. The method of claim 18 wherein the concentration of albumin in the aqueous albumin composition is about 10% w/v to about 25% w/v.

20. The method of claim 18 wherein the concentration of albumin in the aqueous albumin composition is about 25% w/v to about 50% w/v.

21. A method of treating a burned mammal comprising injecting the mammal with an aqueous composition comprising water and about 10% w/v to about 50% w/v oxygenated albumin.

22. The method of claim 21 wherein the concentration of albumin in the aqueous albumin composition is about 10% w/v to about 25% w/v.

23. The method of claim 21 wherein the concentration of albumin in the aqueous albumin composition is about 25% w/v to about 50% w/v.

24. A method of treating a mammal suffering from a condition selected from the group consisting of hypovolemia, trauma, hypoproteinemia, respiratory distress syndrome, burns, acute gastrointestinal hemorrhage, renal dialysis, erythrocyte resuspension, sequestration of protein-rich fluids, malabsorption, cirrhosis, liver failure, nephrosis, neonatal hemolytic disease, a cerebral vascular accident, and ischemia, comprising injecting the mammal with an aqueous albumin composition comprising water and about 10% w/v to about 50% w/v oxygenated albumin.

25. The method of claim 24 wherein the concentration of albumin in the aqueous albumin composition is about 10% w/v to about 25% w/v.

26. The method of claim 24 wherein the concentration of albumin in the aqueous albumin composition is about 25% w/v to about 50% w/v.

* * * * *